(12) United States Patent
Eckert et al.

(10) Patent No.: US 7,613,348 B2
(45) Date of Patent: Nov. 3, 2009

(54) MEDICAL IMAGING SYSTEM HAVING AN APPARATUS FOR COMPRESSING IMAGE DATA

(75) Inventors: Wieland Eckert, Fürth (DE); Frank Fischer, Erlangen (DE); Joachim Hornegger, Effeltrich (DE); André Kaup, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 718 days.

(21) Appl. No.: 11/333,610

(22) Filed: Jan. 17, 2006

(65) Prior Publication Data

US 2006/0171575 A1 Aug. 3, 2006

(30) Foreign Application Priority Data

Jan. 31, 2005 (DE) ............... 10 2005 004 471

(51) Int. Cl.
*G06K 9/36* (2006.01)
(52) U.S. Cl. ............... 382/232; 382/128; 382/132; 382/260
(58) Field of Classification Search ........... 382/128, 382/232, 132, 260, 264, 275; 250/390.02; 378/98.8, 98.2; 348/E7.061; 703/2; 341/107, 341/109; 715/716
See application file for complete search history.

(56) References Cited

U.S. PATENT DOCUMENTS

| | | | |
|---|---|---|---|
| 4,433,428 A | 2/1984 | Haendle et al. | |
| 4,709,385 A | 11/1987 | Pfeiler et al. | |
| 5,481,279 A | 1/1996 | Honda et al. | |
| 6,205,199 B1 * | 3/2001 | Polichar et al. | ............ 378/98.8 |
| 6,520,910 B1 | 2/2003 | Kohls | |
| 6,847,737 B1 * | 1/2005 | Kouri et al. | ................. 382/260 |
| 7,272,265 B2 * | 9/2007 | Kouri et al. | ................. 382/260 |

FOREIGN PATENT DOCUMENTS

| | | |
|---|---|---|
| DE | 31 24 583 A1 | 12/1982 |
| DE | 38 14 089 A1 | 11/1988 |
| DE | 199 05 047 A1 | 8/2000 |
| DE | 101 50 364 A1 | 4/2002 |
| EP | 0 193 712 A1 | 9/1986 |

\* cited by examiner

*Primary Examiner*—Anh Hong Do

(57) ABSTRACT

The invention relates to a medical imaging system having a generation apparatus for continuous image data from successive examination images, having an encoding apparatus for the image data for the purpose of compression on the basis of the method of prediction, having an evaluation apparatus for physiological, periodic data for the purpose of determining the repetition rate thereof, and having a memory apparatus for the compressed image data, where the encoding apparatus is connected to the evaluation apparatus, which controls the latter such that the prediction is matched dynamically to the period length of the physiological data. The use of the information from the ECG signal, for example, for the purpose of compressing the original material provides a dynamic frame rate and also the opportunity to control the dependencies of the prediction such that a minimal memory requirement is obtained without loss of data.

11 Claims, 4 Drawing Sheets

MEDICAL IMAGING SYSTEM HAVING AN APPARATUS FOR COMPRESSING IMAGE DATA

CROSS REFERENCE TO RELATED APPLICATIONS

This application claims priority to the German Application No. DE 10 2005 004 471.9, filed Jan. 31, 2005 which is incorporated by reference herein in its entirety.

FIELD OF INVENTION

The invention relates to a medical imaging system having a generation apparatus for continuous image data from successive examination images, having an evaluation apparatus for physiological, periodic data and having a memory apparatus for the image data.

BACKGROUND OF INVENTION

U.S. Pat. No. 4,709,385 describes an X-ray diagnostic device of this type in which images of a complete cardiac cycle are read into an image store under ECG control as a mask scene. This means that in fluoroscopic examination mode it is possible to overlay the current video signal with the vessel system's stored video signal which belongs to the same cardiac phase. Such an apparatus is used in scout technology (Road Map).

In cardiology, the beating heart is frequently depicted using X-ray radiation and is stored in electronic form as an image sequence. In this case, the volumes of data which arise may be very large. With an entirely usual resolution of 1024×1024 picture elements and a bit depth of 12 bits—according to a resolution for the brightness in 4096 shades of gray—each image requires at least 1.5 MB. With a frame frequency of up to 30 frames per second in cardiology, or up to 60 frames per second in paediatric cardiology, and a recording period of 10 s for one sequence, a data volume of 450 MB or 900 MB is obtained very quickly. While this volume of data can be regarded as "volatile", that is to say is buffer-stored only on the X-ray installation itself, it is still possible to handle the volume using current technology. However, as soon as there is the thought of long-term storage and archiving for 20 years or more, logistical problems quickly arise which are dependent on the volume of the cardiological recordings.

Methods for compressing images are known and widespread in image processing. In this case, a distinction needs to be drawn between "lossless" and "lossy" compression. In the case of lossless compression, it is always possible to restore the full, bit-identical image information from the compressed material, whereas in the case of lossy compression only an approximately identical image can be reconstructed. For processing and transporting medical images, the "DICOM" standard is very widespread and accepted by the leading manufacturers of imaging medical products, including in the transmission and storage of cardiological image sequences. The DICOM standard allows not only encoding in the original format and the associated large volumes of data but also lossless compression using the "JPEG lossless" method. This method compresses each individual image in the sequence independently. In typical use, "JPEG lossless" achieves a compression rate of 2:1 to 3:1, that is to say that the compressed data records require less than half of the original space requirement. Lossy compression methods are currently not yet licensed for use on medical image material, for regulatory reasons. It can be expected that particular lossy methods will also be licensed in the near future.

Another approach is to record the fluoroscopic-examination or recording sequences using a conventional video recorder, traditionally through analog recording of a PAL or NTSC converted and undersampled image signal. A reduction in quality is already accepted for this method, and bit-accurate reproduction of the original material is no longer possible. Digital recording with a reproducible result is therefore preferable over analog recording.

SUMMARY OF INVENTION

Traditionally, a video sequence is divided into single "frames", with each frame containing the actual image information for a particular time. Lining up the frames and playing them back at a particular, prescribed or dynamic frame rate gives the eye the impression of a moving picture. Frames can now be encoded in different ways. In the simplest case, the full image information is stored for each frame, i.e. each frame individually can be shown. This type of encoding takes up a relatively large amount of memory. In the case of moving pictures, it can quickly be seen that there are only relatively small differences between a frame and the direct subsequent frame. If just this difference information is now stored, the data rate can be significantly reduced, but without losing information. Hence, the standardized "MPEG" methods, for example, use not only the I frames (intra-coded), which contain the full image information, but also P frames (predicted frame, inter-coded), which contain only difference information, which means that the full image information can be reconstructed only together with I frames. This method is used generally in the film industry. In the widely used encoding of feature films using MPEG, I frames are used at predefined, regular intervals, as can be seen in FIG. 1. Between the I frames, the significantly space-saving P frames or else, as FIG. 2 shows, B frames with bidirectional prediction are used.

The invention is based on the object of designing a medical imaging system and a method of the type mentioned at the outset such that optimum prediction for compression takes place.

The invention achieves the object for the system by virtue of the evaluation apparatus for physiological, periodic data determining the repetition rate thereof, with the imaging system having an encoding apparatus for the image data for the purpose of compression on the basis of the method of prediction, and the encoding apparatus being connected to the evaluation apparatus, which controls the latter such that the prediction is matched dynamically to the period length of the physiological data. The use of the information from the ECG signal, for example, for the purpose of compressing the original material provides a dynamic frame rate and also the opportunity to control the dependencies of the prediction such that a minimal memory requirement is obtained without loss of data.

It has been found to be advantageous if the evaluation apparatus controls the encoding apparatus such that the images in the first period of the physiological data are compressed using prediction of the subsequent frame from the directly preceding frame, and that the images in the subsequent periods of the physiological data are compressed using prediction of the subsequent frame from the corresponding frame in the preceding periods of the physiological data.

in the steady state of the encoding apparatus

Advantageously, the encoding apparatus may have a memory for examination images with a capacity of at least one period length of the physiological data, which may be a ring buffer, for example.

Alternatively, the evaluation apparatus may be an ECG evaluation apparatus which determines the heartbeat period using ECG electrodes, or may be connected to respiration sensors which detect the breathing period.

The invention achieves the object by means of a method for compressing continuous image data from successive medical examination images on the basis of the method of prediction, which can be controlled on the basis of physiological data such that a dynamic frame rate which is dependent on the period length of the physiological data is obtained.

Advantageously, the physiological data may be derived from the ECG signal and/or from the breathing.

It has been found to be advantageous if the images in the first heartbeat period are compressed using prediction of the subsequent frame from the directly preceding frame, and the images are compressed in the steady state of the encoding apparatus using prediction of the subsequent frame from the corresponding frame in the preceding heartbeat period.

BRIEF DESCRIPTION OF THE DRAWINGS

The invention is explained in more detail below using exemplary embodiments which are shown in the drawing, in which.

DETAILED DESCRIPTION OF INVENTION

Figure 1:
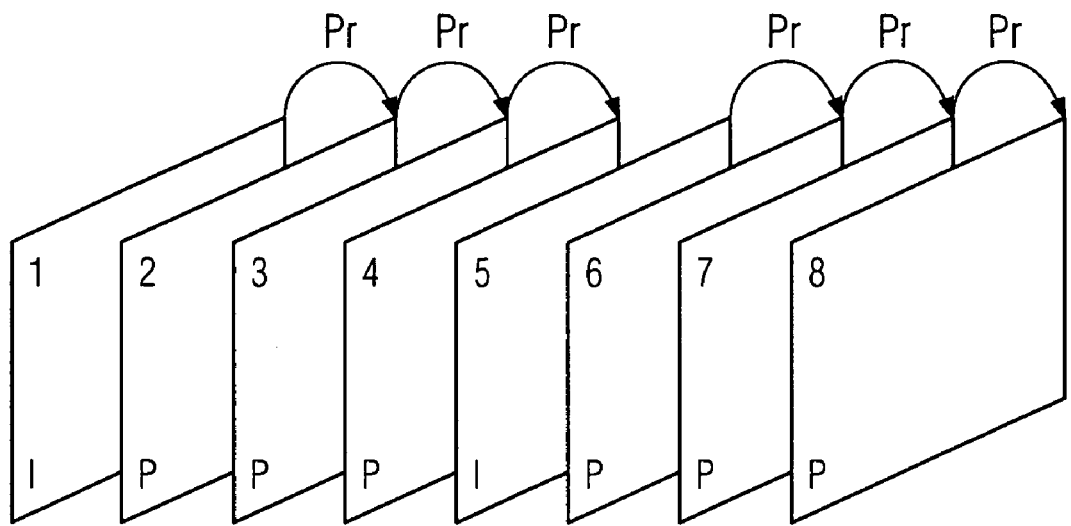
FIG. 1 shows an explanation of MPEG encoding using IPPP frames.
Figure 2:
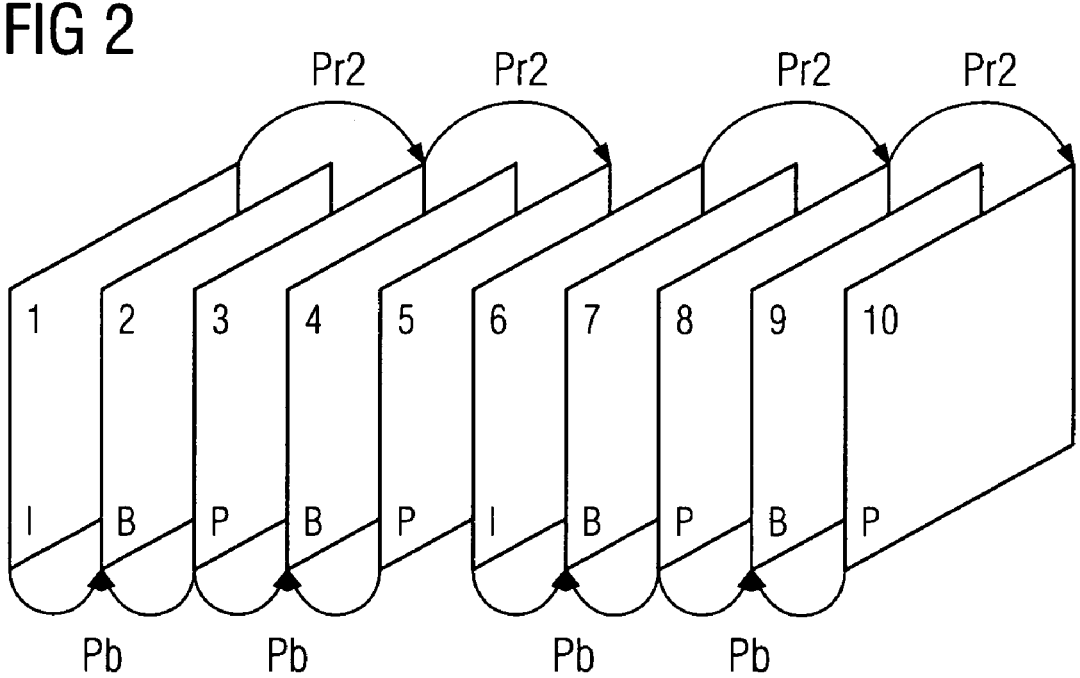
FIG. 2 shows an explanation of the MPEG encoding using IBPBP frames.
Figure 3:
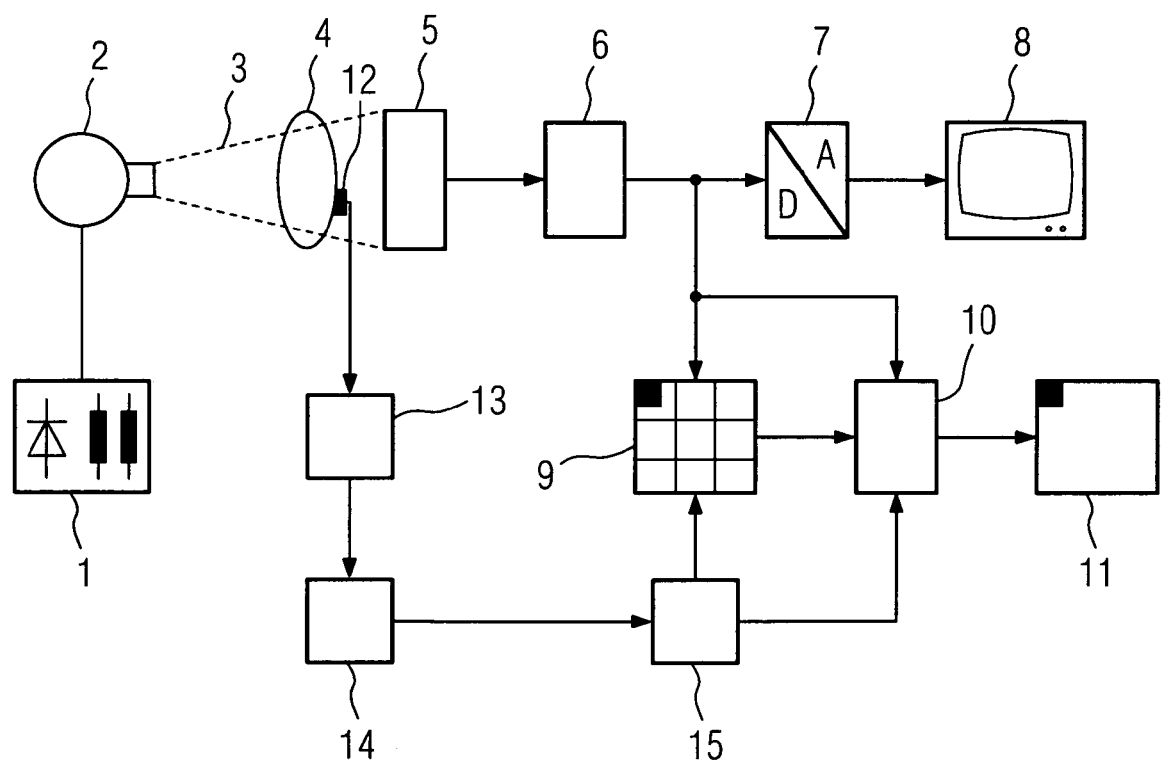
FIG. 3 shows a circuit arrangement of an inventive X-ray diagnostic device.

FIG. 3 shows an inventive X-ray diagnostic device with a high-voltage generator 1 which powers an X-ray tube 2, in whose beam path 3 a patient 4 is situated. Arranged downstream in the beam path 3 is an X-ray detector 5, whose output signal is supplied via a preprocessing stage 6 to a digital/analog converter (D/A converter 7), whose analog output signal is shown as the current X-ray image on a monitor 8.

The output signal from the preprocessing stage 6 is also read into an image store 9, which has a storage capacity of several frames. The image store 9 has a video encoder 10 connected to it as an encoding apparatus, which compresses the video signal for long-term storage in a memory apparatus 11 on the basis of a method with prediction, which is described below.

The patient 4 is fitted with ECG electrodes 12 which are connected to an ECG circuit 13. The ECG signal from the ECG circuit 13 is supplied to a discriminator 14 for the amplitude and phase of the ECG signal. The discriminator 14 is connected to a control apparatus 15 which controls the storage operation in the image store 9 and also the compression in the video encoder 10. The ECG circuit 13, the discriminator 14 and the control apparatus 15 may have the design described in U.S. Pat. No. 4,433,428, for example.

When the fluoroscopy has been turned on, the digital video signals which are present at the output of the X-ray detector 5 are read into a storage location in the image store 9 over at least one cardiac cycle.

Following the appearance of an identification feature of the ECG, for example the R peak, recordings which are associated with different cardiac phases in a cardiac cycle are successively stored in the image store 9. When storage is ended, the frames held in the image store 9 are read with the current video signal in sync with the cardiac phases and are encoded in the video encoder 10.

For the purpose of simpler explanation, the text below uses the terminology of MPEG encoding.

For encoding such cardiological X-ray sequences, use is made of the periodicity of the original material. The change in the image information which is brought about by the heartbeat is ideally periodical, i.e. after a particular time t he objects which are visible in the image have adopted an almost identical position again. In other words, it is expected that the difference between the current frame and the frame which was taken exactly one heartbeat period beforehand will be very small. The small differences can now be encoded in very compact and space-saving fashion. This achieves a high compression rate.

Figure 4:
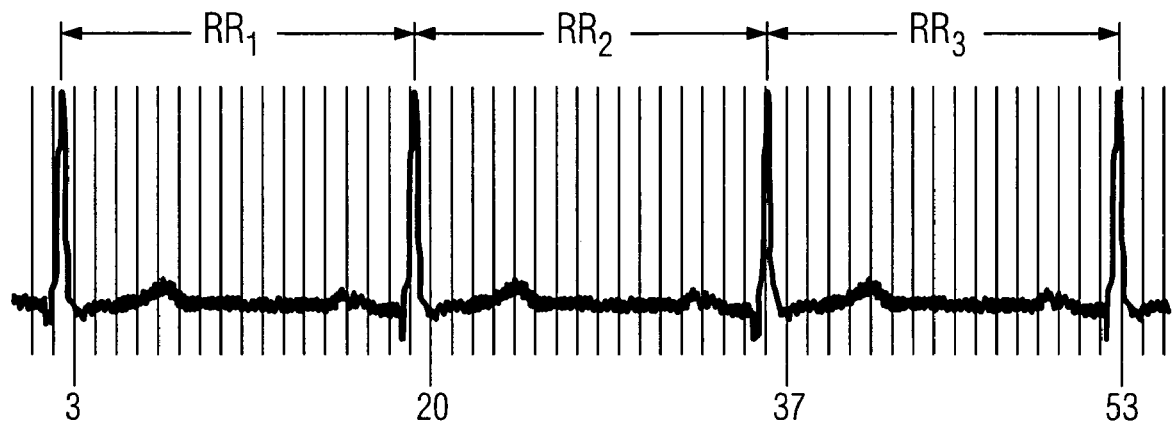
FIG. 4 shows an illustration of an ECG signal profile with period length and associated frame number.

In contrast to the encoding of feature films, there are thus no prescribed, fixed intervals used for I flames, but rather the information about the period of the patient's heartbeat. The information about the heartbeat is obtained from an electrocardiogram (ECG) which is taken during the examination and from which the period can be read off very easily. FIG. 4 shows an example of an ECG signal and the associated frame numbers. It also shows the period lengths.

Figure 5:
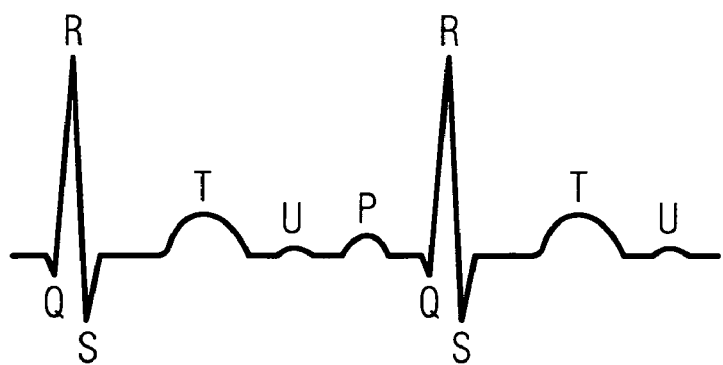
FIG. 5 shows an idealized profile of an ECG period.

The ECG is evaluated automatically. The period length is determined using a detection method which ascertains the times of the most prominent features of the ECG signal, known as the "QRS complexes". In this context, the period of time from one QRS complex to the next describes precisely one heartbeat period, which is shown in FIG. 5. In the literature, various methods for determining the heart rate, that is to say the interval between successive QRS complexes, have been known for a long time. Such methods can be used in the present invention.

Figure 6:
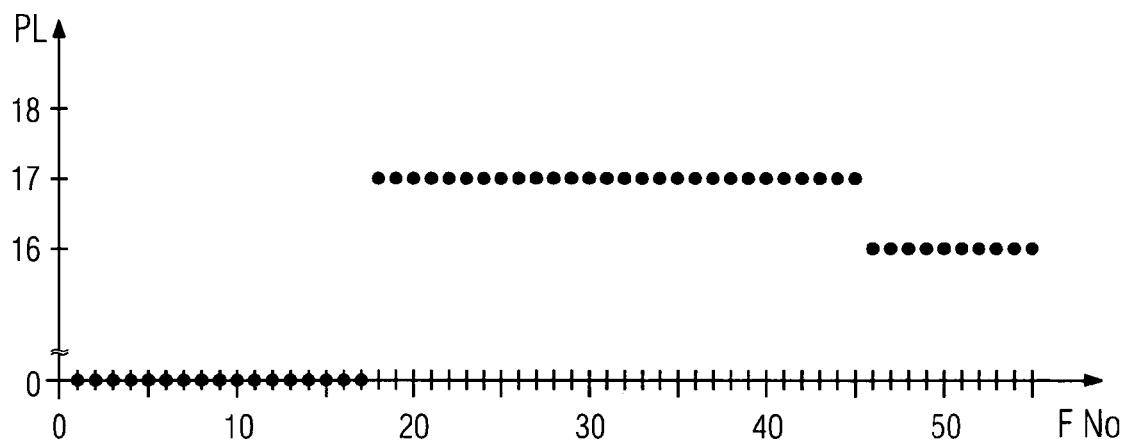
FIG. 6 shows an illustration of the ascertained period length, related to the signal in FIG. 4.

Since the recorded ECG signal and the X-ray image sequence are in sync with one another, it is possible to associate each time in the ECG clearly with precisely one frame. FIG. 6 now shows the calculated period length and, for each frame, shows the distance from that frame which was taken precisely one period beforehand. For the first incomplete period, a heart rate is not yet known, which is represented by the value 0.

The essence of the invention is now based on the observation that the difference between the image information in a frame and that frame which was precisely one heartbeat beforehand is minimal. The movement of the cardiac muscle is observed at two times at which the muscle respectively adopts the same position and the same space. For this reason, this difference in the image information should ideally be smaller than the difference between a frame and its direct preceding frame.

Figure 7:
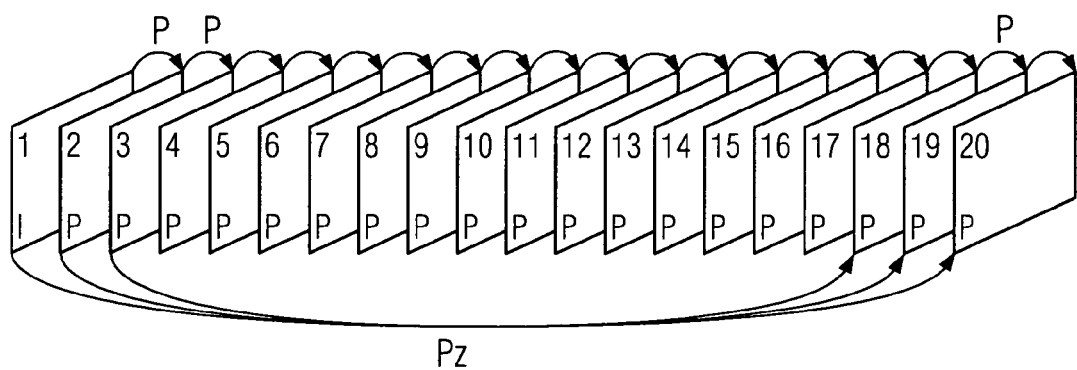
FIG. 7 shows an example of the prediction using the period length of the heartbeat.

The values of the period length, which are ascertained by the ECG evaluation apparatus 12 to 15, expressed in frames, are now routed to the video encoder 10, which, in addition to the directly preceding frame, uses the corresponding frame of the last heartbeat period to predict the next P frame. In FIG. 7, only the respective predecessor up to frame number 18 is used for the prediction Pr. After frame number 18, the information from the heart rate can be used and the frame from the respective previous period can be used as reference frame for the prediction Pz.

The MPEG 4/AVC standard already allows a prediction from a plurality of preceding frames ("multiple reference frames" technology), but with just the direct predecessors being taken into account. Every additional reference frame also increases the computation complexity. In the method described here, only two frames are initially used for the prediction, the direct predecessor frame and the corresponding frame from the last period, for reasons of computation time. It goes without saying that it is also possible to take more candidates than reference frames into account, for example the neighbors to the frame in the previous period etc.

In particular, the decision regarding whether an I frame or a P frame is encoded is not determined from the outset either, but rather is ascertained on the basis of the data material during the encoding.

The inventive method is independent of the frame frequency of the material. The technical repetition rate of, by way of example, 30 frames per second (fps) is not used for the compression, but rather the "physiological repetition rate", which is given by the periodicity of the heartbeats and has been recorded by the ECG.

To implement the method, an image store 9 is preferably used, which can record at least one period length and image data, even if just one frame is predicted in each case. This image store 9 may be implemented as a ring buffer, for example, in which the respective oldest frame is discarded for each new frame added.

In our first implementation, the results of the method described in this invention even comply with the existing H.264/AVC standard, and the sequences compressed therewith can be shown by any H.265/AVC compatible players.

A fundamental feature of the invention is thus the use of the information from the ECG signal to compress the original material.

In another use for the method presented here, it is also possible to use the periodicity of the breathing. Respiration causes visible movement of the thorax and of the ribs in the X-ray sequence. Synchronization with the breathing rate can thus achieve a similar effect to synchronization with the heart rate, but with a comparatively much longer recording time being required in order to ascertain and use the period length. The period length of the breathing can be estimated from the envelope of the ECG signal, for example, or can be recorded by other respiration measuring devices in sync with the X-ray sequence.

In addition, it is also possible to ascertain the superposition of the two movements and to use it to determine a reference frame. Since both the contraction of the cardiac muscle and the breathing are periodic, the best candidate for a reference frame is even the one in which both the "phase" of the ECG and the phase of the respiration match the phase of the frame which is currently being considered. In practice, however, it will be necessary to consider very large distances in this specific use and to invest a relatively large amount of effort in computation time and storage involvement.

The inventive method allows a higher compression factor to be achieved, for the same image information, than with the previously used methods. Various advantages are obtained for the systems involved.

The cardiological X-ray system creates the original material. The necessary data rates and volumes can be reduced as appropriate when compression is increased. For a given size of data store, correspondingly more patients can thus be examined before transfer to an archive system is necessary. The reduced data rates also result in lower demands on the internal data paths in the X-ray system and hence in lower procurement costs for the recording system.

The clinic's archive system needs to ensure long-term archiving of the examination results. The scope of the archive grows constantly with the number of examinations. The fact that the data are compressed better means that the gradient of growth is shallower, i.e. the next expansion stage for the archive system occurs at a later time than with uncompressed storage. Less growth means that the ongoing costs of archiving are reduced.

Transfer of the data, e.g. from the recording system to the archive or from the archive to the findings station, is speeded up. The fact that the data can be compressed to a greater extent means that the transfer time is reduced for a given bandwidth on the clinic's network. For the clinical user, the faster reaction results in an improved workflow. The shorter reaction time increases acceptance with the user.

The invention claimed is:

1. A medical imaging system, comprising:
   an image generation device for generating continuous image data from successive medical examination images;
   an encoding device for compressing the image data using a prediction method;
   an evaluation unit for evaluating physiological periodic data regarding a repetition rate related to the physiological periodic data; and
   a memory device for storing the compressed image data, wherein the encoding device is connected to the evaluation unit, the evaluation unit configured to control the encoding device by adjusting the prediction method relative to a current period length of the physiological periodic data.

2. The medical imaging system as claimed in claim 1, wherein the evaluation apparatus is further configured to control the encoding device such that:
   images of a first period of the physiological periodic data are compressed by predicting a subsequent frame of the first period based on a frame of the first period immediately preceding the subsequent frame, and
   images of subsequent periods of the physiological periodic data are compressed by predicting a subsequent frame of a subsequent period based on a corresponding frame of periods preceding the subsequent period.

3. The medical imaging system as claimed in claim 1, wherein the encoding device includes a memory for storing the medical examination images, the memory having a capacity for storing at least one period of the physiological periodic data.

4. The medical imaging system as claimed in claim 3, wherein the memory is a ring buffer.

5. The medical imaging system as claimed in claim 1, wherein the evaluation unit is configured to evaluate ECG data.

6. The medical imaging system as claimed in claim 1, wherein the evaluation unit is configured to determine a heartbeat period using ECG electrodes.

7. The medical imaging system as claimed in claim 1, wherein the evaluation unit is connected to respiration sensors.

8. A method for compressing continuous image data from successive medical examination images, the method comprising:
   compressing the image data using a prediction method by an encoding device;

adjusting the prediction method based on a period length of physiological data related to the image data by an evaluation unit; and determining a frame rate related to the image data based upon the period length by the evaluation unit.

9. The method as claimed in claim 8, wherein the physiological data are obtained from an ECG signal.

10. The method as claimed in claim 8, further comprising:

compressing image data related to a first heartbeat period by predicting a subsequent frame of the first period based on a frame immediately preceding the subsequent frame; and compressing image data related to a steady state of the encoding device by predicting a subsequent frame of the steady state based on a corresponding frame of such heartbeat period immediately preceding the heartbeat period related to the subsequent frame.

11. The method as claimed in claim 8, wherein the physiological data are related to the breathing of a patient under examination.

* * * * *

UNITED STATES PATENT AND TRADEMARK OFFICE
CERTIFICATE OF CORRECTION

PATENT NO. : 7,613,348 B2  Page 1 of 1
APPLICATION NO. : 11/333610
DATED : November 3, 2009
INVENTOR(S) : Eckert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 962 days.

Signed and Sealed this

Nineteenth Day of October, 2010

David J. Kappos
*Director of the United States Patent and Trademark Office*